US010744351B2

United States Patent
Fujimori et al.

(10) Patent No.: US 10,744,351 B2
(45) Date of Patent: *Aug. 18, 2020

(54) MASK

(75) Inventors: Yoshie Fujimori, Tokyo (JP); Youhei Jikihara, Tokyo (JP); Tetsuya Sato, Tokyo (JP); Yoko Fukui, Tokyo (JP); Tsuruo Nakayama, Tokyo (JP)

(73) Assignee: NBC MESHTEC, INC., Tokyo (JP)

( * ) Notice: Subject to any disclaimer, the term of this patent is extended or adjusted under 35 U.S.C. 154(b) by 752 days.

This patent is subject to a terminal disclaimer.

(21) Appl. No.: 13/395,670

(22) PCT Filed: Sep. 30, 2010

(86) PCT No.: PCT/JP2010/005894
§ 371 (c)(1),
(2), (4) Date: Mar. 23, 2012

(87) PCT Pub. No.: WO2011/040035
PCT Pub. Date: Apr. 7, 2011

(65) Prior Publication Data
US 2012/0192876 A1    Aug. 2, 2012

(30) Foreign Application Priority Data

Sep. 30, 2009   (JP) ................................ 2009-228884

(51) Int. Cl.
*A62B 23/02* (2006.01)
*A61K 33/00* (2006.01)
(Continued)

(52) U.S. Cl.
CPC ............ *A62B 23/025* (2013.01); *A41D 13/00* (2013.01); *A41D 13/05* (2013.01);
(Continued)

(58) Field of Classification Search
CPC ....... A62B 23/02; A62B 23/025; A62B 18/02; A62B 18/025; A62B 7/00–14;
(Continued)

(56) References Cited

U.S. PATENT DOCUMENTS 6,281,515 B1 * 8/2001 Demeo et al. ............. 250/516.1
9,155,309 B2 * 10/2015 Fujimori ................. A61L 31/16
(Continued)

FOREIGN PATENT DOCUMENTS

| JP | 2002-136615 | 5/2002 |
| JP | 2004-313415 | 11/2004 |

(Continued)

OTHER PUBLICATIONS

International Search Report dated Nov. 9, 2010 in International (PCT) Application No. PCT/JP2010/005894, of which the present application is the national stage.
(Continued)

*Primary Examiner* — Keri J Nelson
*Assistant Examiner* — Michelle J Lee
(74) *Attorney, Agent, or Firm* — Wenderoth, Lind & Ponack, L.L.P.

(57) ABSTRACT

A mask is provided that can inactivate viruses adhering thereto even in the presence of lipids and proteins regardless of whether or not the viruses have an envelope. The mask can inactivate viruses adhering thereto and includes a mask body provided with a member used when the mask is worn and virus inactivating fine particles having a virus inactivating ability and held by the mask body. The virus inactivating fine particles are particles of at least one selected from the group consisting of platinum(II) iodide, palladium(II) iodide, silver(I) iodide, copper(I) iodide, and copper(I) thiocyanate.

6 Claims, 4 Drawing Sheets

(51) Int. Cl.
| | |
|---|---|
| *A61K 33/34* | (2006.01) |
| *A61K 33/24* | (2019.01) |
| *A61K 33/38* | (2006.01) |
| *D06M 10/04* | (2006.01) |
| *D06M 10/06* | (2006.01) |
| *D06M 10/08* | (2006.01) |
| *D06M 10/00* | (2006.01) |
| *A62B 18/00* | (2006.01) |
| *A41D 13/00* | (2006.01) |
| *A62B 23/00* | (2006.01) |
| *A62B 18/02* | (2006.01) |
| *A41D 13/11* | (2006.01) |
| *A62B 7/00* | (2006.01) |
| *A41D 13/05* | (2006.01) |
| *A62D 9/00* | (2006.01) |

(52) U.S. Cl.
CPC ...... *A41D 13/1161* (2013.01); *A41D 13/1192* (2013.01); *A61K 33/00* (2013.01); *A61K 33/24* (2013.01); *A61K 33/34* (2013.01); *A61K 33/38* (2013.01); *A62B 7/00* (2013.01); *A62B 18/00* (2013.01); *A62B 18/02* (2013.01); *A62B 18/025* (2013.01); *A62B 23/00* (2013.01); *A62D 9/00* (2013.01); *D06M 10/00* (2013.01); *D06M 10/04* (2013.01); *D06M 10/06* (2013.01); *D06M 10/08* (2013.01)

(58) Field of Classification Search
CPC ........ A62B 18/00–06; A62B 23/00–06; A41D 13/00; A41D 13/05; A41D 13/1161; A41D 13/1192; A41D 13/11–1192; D06M 10/00; D06M 10/04; D06M 10/06; D06M 10/08; D06M 10/10; A62D 9/00; A61K 33/00; A61K 33/24; A61K 33/34; A61K 33/38; A61M 16/0666–0677; A61M 16/0087–0093; A61M 16/06–0694; A61B 16/06–0694; B01D 39/00–2096; Y10T 442/20; Y10T 442/2082; Y10T 442/2115; Y10T 442/2131; Y10T 442/218; Y10T 442/223; Y10T 442/2328; Y10T 442/2525; Y10T 442/259; D60M 10/00; D60M 11/00; D60M 11/83; D60M 10/04; D60M 10/06; D60M 10/08
USPC ............ 128/205.27, 205.28, 205.29, 206.12, 128/206.13, 206.19, 206.27, 206.28, 128/207.11, 863; 2/206, 9, 410, 424; 8/115.51, 108.1, 115.54, 115.55, 115.56, 8/115.6; 424/600, 617, 618, 630, 646, 424/649; 427/2.1, 2.3, 2.31, 376.1, 427/376.2; 55/482, 486; 96/223, 226; 523/122, 203
See application file for complete search history.

(56) References Cited

U.S. PATENT DOCUMENTS

| | | | |
|---|---|---|---|
| 2007/0169278 A1* | 7/2007 | Shigita | D06M 11/63 8/115.51 |
| 2007/0175477 A1* | 8/2007 | Baggett | 128/206.13 |
| 2007/0292486 A1* | 12/2007 | Sen | A61K 33/38 424/443 |
| 2008/0295843 A1 | 12/2008 | Haas | |
| 2009/0078263 A1* | 3/2009 | Ozawa et al. | 128/206.12 |
| 2009/0094954 A1* | 4/2009 | Nakayama | C08J 7/045 55/524 |
| 2009/0130161 A1* | 5/2009 | Sarangapani | A01N 59/16 424/409 |
| 2009/0232962 A1 | 9/2009 | Marcoon | |
| 2011/0232653 A1* | 9/2011 | Imashiro | A41D 13/1192 128/863 |
| 2011/0262513 A1 | 10/2011 | Fujimori et al. | |
| 2012/0171276 A1 | 7/2012 | Fujimori et al. | |

FOREIGN PATENT DOCUMENTS

| | | |
|---|---|---|
| JP | 2004-323430 | 11/2004 |
| JP | 2005-28230 | 2/2005 |
| JP | 2007-021031 | 2/2007 |
| JP | 2008-188082 | 8/2008 |
| JP | 3151082 | 6/2009 |
| KR | 10-2009-0074946 | 10/2011 |
| WO | 2005/083171 | 9/2005 |
| WO | 2009/101930 | 8/2009 |

OTHER PUBLICATIONS

International Preliminary Report on Patentability dated May 8, 2012 in International Application No. PCT/JP2010/005894, of which the present application is the national stage.
U.S. Appl. No. 13/142,118, filed Jun. 24, 2011.
U.S. Appl. No. 13/395,691, filed Mar. 23, 2012.
Extended European Search Report dated Mar. 29, 2016 in corresponding European Application No. 10820156.7.

* cited by examiner

MASK

TECHNICAL FIELD

The present invention relates to a mask, and particularly to a mask that can inactivate various viruses adhering thereto even in the presence of lipids and proteins regardless of whether or not the viruses have an envelope.

BACKGROUND ART

In recent years, deaths have been reported that are caused by infections with new types of viruses such as SARS (severe acute respiratory syndrome) and avian influenza. At present, because of developments in transportation and mutations of viruses, the world faces the risk of a "pandemic" that is an epidemic of viral infection throughout the world, and there is an urgent need for countermeasures. To deal with such a situation, the development of vaccine-based antiviral drugs is hastened. However, since vaccines have their own specificity, they can only prevent infection with specific viruses. Moreover, preparation of vaccines for the new types of viruses needs a considerable amount of time.

To prevent infection with such viruses, it is recommended to wear a mask. However, the problem with wearing a mask is that secondary infection may occur because viruses adhering to the used mask may adhere to hands when the mask is disposed of. Therefore, a mask is of little use in preventing infection perfectly.

To solve the foregoing problem, masks having the effect of inactivating viruses (reducing the infectivity of the viruses or deactivating the viruses) have been proposed (for example, Patent Literatures 1 and 2). Patent Literature 1 proposes a mask having the effect of inactivating bacteria and viruses. More specifically, iodine is adsorbed on anion exchange fibers prepared by bonding ion exchangeable functional groups such as amino groups to the fiber matrix, and a cloth containing the iodine-adsorbed fibers is used for the body of the mask. In a mask in Patent Literature 2, a cloth supporting a component extracted from *Sasa veitchii* and an inorganic porous material is used for the body of the mask to impart the effect of inactivating viruses to the mask.

CITATION LIST

Patent Literature

Patent Literature 1: Japanese Patent Application Laid-Open No. 2005-28230

Patent Literature 2: Japanese Patent Application Laid-Open No. 2004-323430

SUMMARY OF INVENTION

Technical Problem

Although Patent Literature 1 shows that the mask has an effect on bacteria such as *Escherichia coli*, no examples are given for viruses. Therefore, it is not known whether or not the mask has the effect of inactivating viruses.

In an example in Patent Literature 2, an antiviral test on the mask is shown. However, the virus used in the test is an RS (Respiratory Syncytial) virus having an envelope. Viruses can be classified into those having no envelope such as noroviruses and those having an envelope such as influenza viruses. Even though a drug can inactivate viruses having an envelope, this drug may not be effective for viruses having no envelope. In Patent Literature 2, no examples of the mask are described for viruses having no envelope. Therefore, it is not known whether or not the mask has the same effect on viruses having no envelope.

A mask is an article used to cover the mouth and nose of the wearer, and lipids and proteins contained in bodily fluids such as saliva may adhere to the mask. Therefore, it is preferable that the mask can inactivate viruses even in an environment in which lipids and proteins are present. However, the mask in Patent Literature 2 is not tested in such an environment.

To solve the foregoing problems, the present invention provides a mask that can inactivate viruses adhering thereto even in the presence of lipids and proteins regardless of whether or not the viruses have an envelope.

Solution to Problem

A first aspect of the present invention provides a mask that can inactivate a virus adhering thereto, the mask characterized by comprising: a mask body provided with a member used when the mask is worn; and virus inactivating fine particles having an ability to inactivate viruses and held by the mask body, the virus inactivating fine particles being particles of at least one selected from the group consisting of platinum(II) iodide, palladium(II) iodide, silver(I) iodide, copper(I) iodide, and copper(I) thiocyanate.

A second aspect of the invention is the mask according to the first aspect, characterized in that the virus inactivating fine particles are fixed to the mask body at least through a silane monomer and/or a polymerization product of the silane monomer.

A third aspect of the invention is the mask according to the first aspect, characterized in that the virus inactivating fine particles are held by the mask body through groups of other inorganic fine particles that are fixed to the mask body through chemical bonds with a silane monomer and/or a polymerization product of the silane monomer.

A fourth aspect of the invention is the mask according to any of the first to third aspects, characterized in that the mask body includes a plurality of breathable filter members stacked in a thickness direction of the mask body, and the virus inactivating fine particles are held by at least one of the plurality of filter members constituting the mask body.

A fifth aspect of the invention is the mask according to the fourth aspect, characterized in that the virus inactivating fine particles are held at least by a filter member that is located on the innermost side when the mask is worn.

A sixth aspect of the invention is the mask according to the fourth or fifth aspect, characterized in that the virus inactivating fine particles are held at least by a filter member that is located on the outermost side when the mask is worn.

A seventh aspect of the invention is the mask according to any of the first to sixth aspects, characterized in that an average diameter of the virus inactivating fine particles is 1 nm or larger and smaller than 500 nm.

Advantageous Effects of Invention

According to the present invention, there is provided a mask that can easily inactivate various viruses such as viruses surrounded by a membrane referred to as an envelope containing a lipid and viruses having no envelope, and that can inactivate the viruses even in the presence of, in addition to the viruses, lipids and proteins resulting from, for example, the adhesion of droplets.

DESCRIPTION OF EMBODIMENTS

Figure 1:
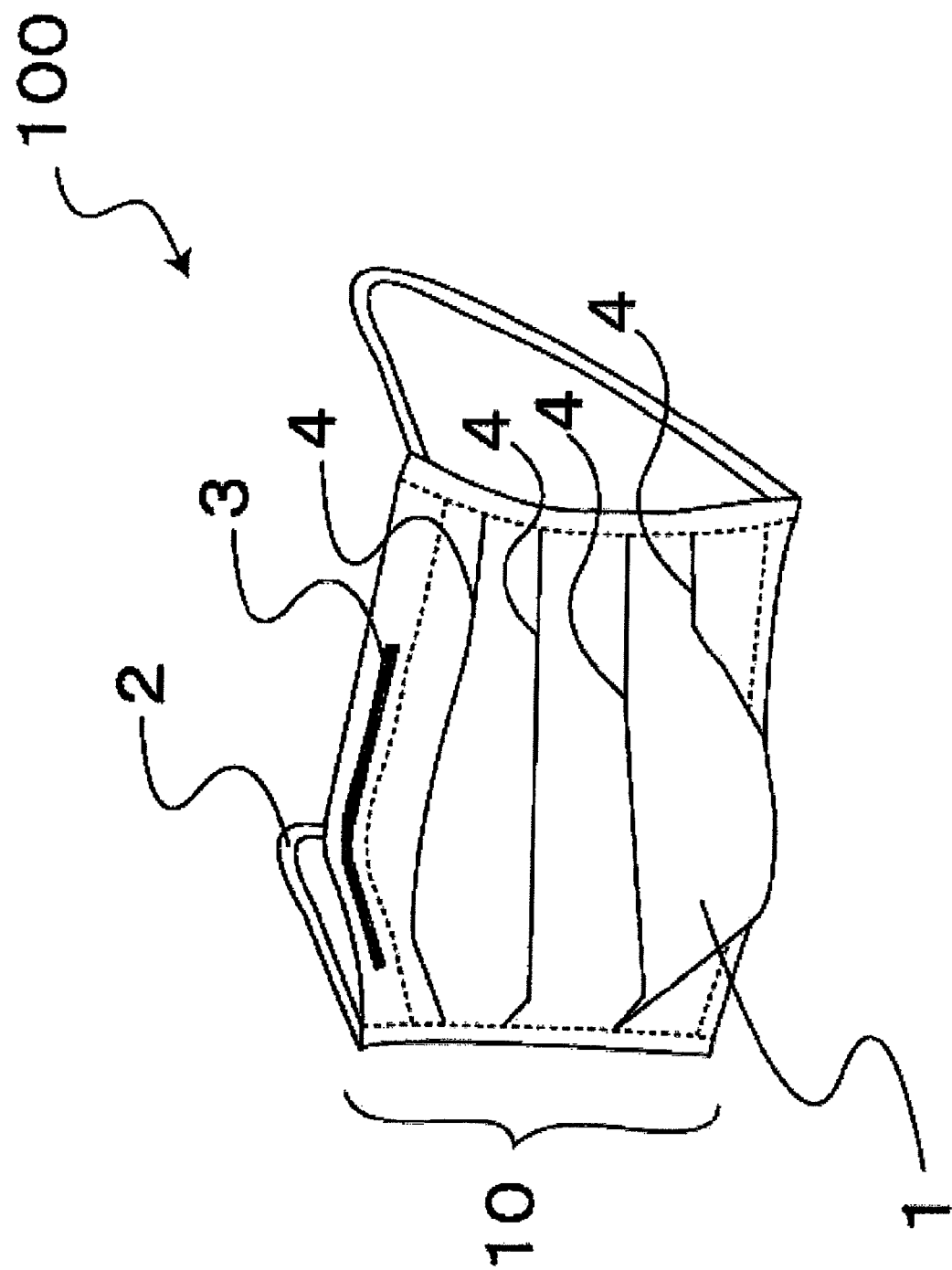
FIG. 1 is a perspective view of a mask of a first embodiment.

A first embodiment will next be specifically described with reference to FIG. 1.

First, the general configuration of a mask 100 of the first embodiment that can inactivate viruses will be described. The mask 100 of the first embodiment includes a mask body 10 having a substantially rectangular shape and rubber cords 2 (corresponding to members used when the mask is worn) that are sewed onto both ends of the lengthwise edges of the mask body 10 and are to be stretched around ears.

Figure 2:
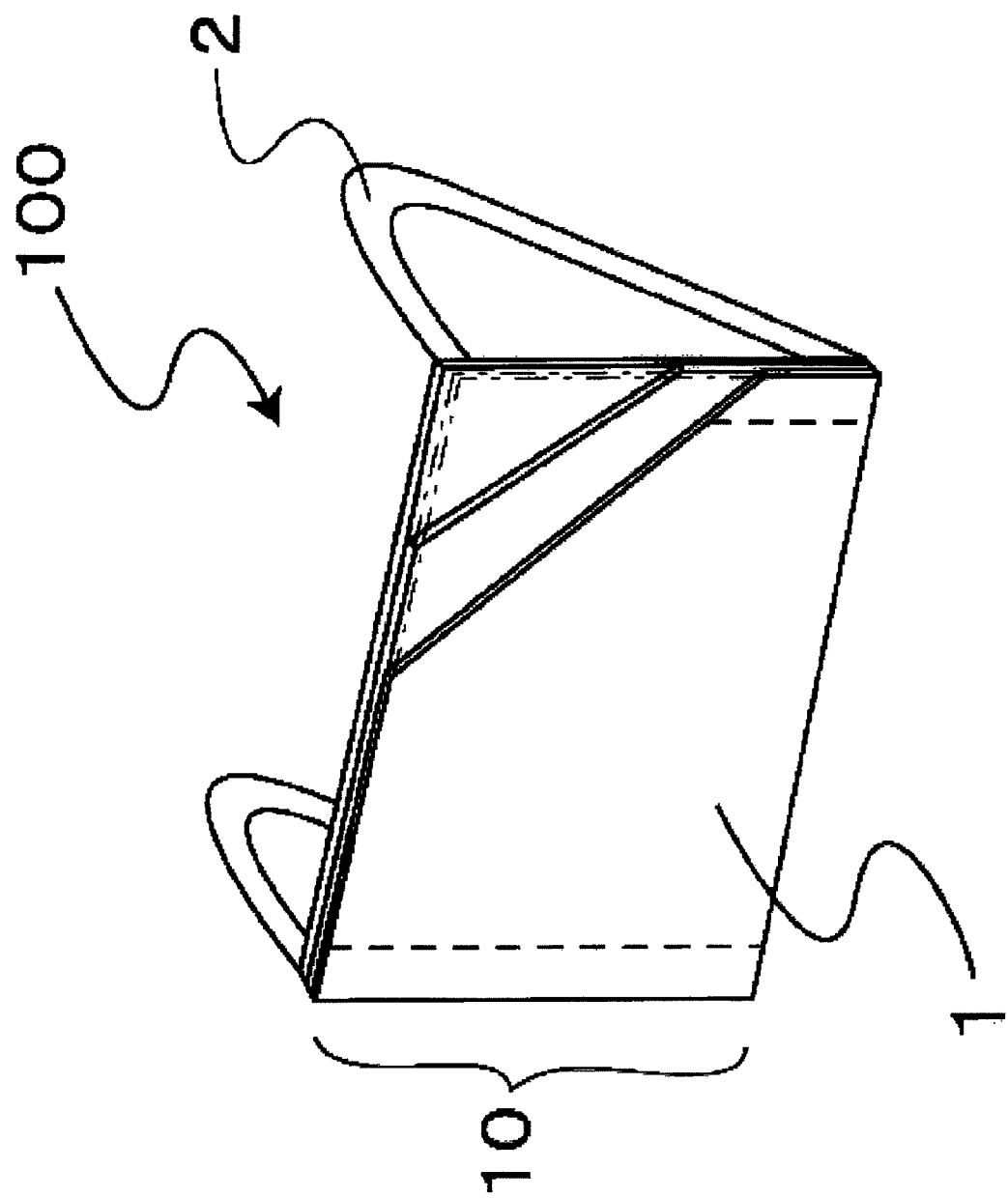
FIG. 2 is a partially cut-away perspective view of the mask of the first embodiment.

As shown in FIG. 2, in the first embodiment, the mask body 10 includes a plurality of (three in the first embodiment) breathable filter members 1, and the filter members 1 are stacked in the thickness direction of the mask body 10 and integrated by welding. As shown in FIG. 1, several (four in the first embodiment) pleats 4 extending in the lengthwise direction are formed in the mask body 10 so that the mask body can freely change its width according to the size of the face of the wearer. The pleats 4 can open in a vertical direction, so that three-dimensional spaces are formed in front of the nose and mouth. Therefore, the contact of the mask with the mouth and nose is loosened. This facilitates respiration and reduces the amount of cosmetics adhering to the mask. The above-described integrating processing is not limited to the welder bonding, and any other method such as sewing may be used. In FIG. 2, for the purpose of facilitating understanding, the pleats 4 and a band-shaped wire 3 described later are omitted from the figure. In FIG. 2, for the purpose of facilitating the understanding of the present application, the plurality of filter members 1 are shown. However, this is only an example, and the filter member 1 may be composed of a single layer.

The band-shaped wire 3 made of a bendable metal or resin is inserted into the upper edge of the mask body 10. The formation of a gap between the mask 100 of the first embodiment and the nose of the wearer can be prevented by bending the band-shaped wire 3 so as to extend along the shape of the nose of the wearer. Therefore, problems such as fogging of eyeglasses by breath and intrusion of viruses together with external air through the gap can be resolved.

A description will next be given of the filter member 1 constituting the mask body 10. As described above, in the first embodiment, the three filter members 1 are stacked in the thickness direction of the mask body 10. Virus inactivating fine particles having a virus inactivating ability are bonded, at least through a silane monomer or an oligomer obtained by polymerization of the silane monomer, to the outer surfaces of the filter members 1 that are located on the outermost and innermost sides in the thickness direction, i.e., are located on the outermost and innermost sides during wearing of the mask. No particular limitation is imposed on the dimensions of the filter member 1, and a person skilled in the art can appropriately set the dimensions. For example, the dimensions of the filter member 1 for adults may be different from those for kids. When the filter member 1 is composed of a single layer, the virus inactivating fine particles are bonded to both sides of the filter member 1.

In the first embodiment, the virus inactivating fine particles are fine particles of at least one inorganic compound selected from the group consisting of platinum(II) iodide, palladium(II) iodide, silver(I) iodide, copper(I) iodide, and copper(I) thiocyanate and can inactivate viruses regardless of whether or not the viruses have an envelope. Therefore, the mask 100 of the first embodiment can be considered to hold an antiviral agent including fine particles of at least one inorganic compound selected from the group consisting of platinum(II) iodide, palladium(II) iodide, silver(I) iodide, copper(I) iodide, and copper(I) thiocyanate. The virus inactivating fine particles according to the first embodiment can inactivate viruses even in the presence of proteins and lipids.

At present, the virus inactivating mechanism of the virus inactivating fine particles is not clear. The mechanism is assumed to be as follows. When the virus inactivating fine particles come into contact with moisture in air or droplets, part of the virus inactivating fine particles undergoes an oxidation-reduction reaction. This causes some effect on the surface electric charge or membrane protein or DNA of the viruses adhering to the mask 100 of the first embodiment, and the viruses are thereby inactivated.

No particular limitation is imposed on the size of the held virus inactivating fine particles, and a person skilled in the art can appropriately set the size. However, the average particle diameter is preferably 1 nm or larger and smaller than 500 nm. When the average particle diameter is smaller than 1 nm, the virus inactivating fine particles are physically unstable and agglutinate with each other. Therefore, it is difficult to fix the particles on the filter member 1 uniformly. When the average particle diameter is 500 nm or larger, the adhesion between the particles and the filter member 1 is lower than that when the average particle diameter falls within the above range. In the present description, the average particle diameter is a volume average particle diameter.

In the first embodiment, the virus inactivating fine particles are fixed to the filter member 1 through a binder. No particular limitation is imposed on the binder used. The molecular weights of the silane monomer and oligomer obtained by polymerization of the silane monomer are low. Therefore, these monomer and oligomer are preferred because the contact between the virus inactivating fine particles and viruses is less likely to be prevented, and the viruses can be effectively inactivated. In addition, since the adhesion of the binder to the filter member 1 used as substrates is improved by using the silane monomer and/or the oligomaer as the binder, the virus inactivating fine particles can be more stably supported on the filter member 1.

Specific examples of the silane monomer used for the mask 100 of the first embodiment include silane monomers represented by a general formula $X—Si(OR)_n$ (n is an integer of from 1 to 3). X is a functional group that reacts with an organic material, and examples thereof include a vinyl group, an epoxy group, a styryl group, a methacryl group, an acryloxy group, an isocyanate group, a polysulfide group, an amino group, a mercapto group, and a chloro group. Each OR is a hydrolyzable alkoxy group such as a methoxy group or an ethoxy group, and the three functional groups in the silane monomer may be the same or different. These alkoxy groups including methoxy and ethoxy groups are hydrolyzed to form silanol groups. The reactivity of such a silanol group, a vinyl group, an epoxy group, a styryl group, a methacryl group, an acryloxy group, an isocyanate group, and functional groups having an unsaturated bond and the like is known to be high. More specifically, in the mask 100 of the first embodiment, the virus inactivating fine particles are firmly held on the surface of the filter member 1 by the chemical bonds through the silane monomer having high reactivity.

Examples of the silane monomer represented by the above general formula include vinyltrichlorosilane, vinyltrimethoxysilane, vinyltriethoxysilane, vinyltriacetoxysilane, N-β-(N-vinylbenzylaminoethyl)-γ-aminopropyltrimethoxysilane, a hydrochloride of N-(vinylbenzyl)-2-aminoethyl-3-aminopropyltrimethoxysilane, 2-(3,4 epoxycyclohexyl)ethyltrimethoxysilane, 3-glycidoxypropyltrimethoxysilane, 3-glycidoxypropylmethyldiethoxysilane, 3-glycidoxypropyltriethoxysilane, p-styryltrimethoxysilane, 3-methacryloxypropylmethyldimethoxysilane, 3-methacryloxypropyltrimethoxysilane, 3-methacryloxypropylmethyldiethoxysilane, 3-methacryloxypropyltriethoxysilane, 3-acryloxypropyltrimethoxysilane, 3-isocyanatepropyltriethoxysilane, bis(triethoxysilylpropyl)tetrasulfide, 3-aminopropyltrimethoxysilane, 3-aminopropyltriethoxysilane, 3-triethoxysilyl-N-(1,3-dimethyl-butylidene)propylamine, N-phenyl-3-aminopropyltrimethoxysilane, N-2-(aminoethyl)-3-aminopropylmethyldimethoxysilane, N-2-(aminoethyl)-3-aminopropyltrimethoxysilane, N-2-(aminoethyl)-3-aminopropyltriethoxysilane, 3-mercaptopropylmethyldimethoxysilane, 3-mercaptopropyltrimethoxysilane, N-phenyl-3-aminopropyltrimethoxysilane, special aminosilanes, 3-ureidopropyltriethoxysilane, 3-chloropropyltrimethoxysilane, tetramethoxysilane, tetraethoxysilane, methyltrimethoxysilane, methyltriethoxysilane, dimethyldiethoxysilane, phenyltriethoxysilane, hexamethyldisilazane, hexyltrimethoxysilane, decyltrimethoxysilane, hydrolyzable group-containing siloxanes, fluoroalkyl group-containing oligomers, methylhydrogensiloxane, and silicone quaternary ammonium salt.

Examples of the silane-based oligomers include commercially available oligomers KC-89S, KR-500, X-40-9225, KR-217, KR-9218, KR-213, and KR-510, which are all products of Shin-Etsu Chemical Co., Ltd. These silane-based oligomers may be used alone, as a mixture of two or more thereof, or as a mixture with one or two or more of the above-described silane monomers.

In the mask 100 of this embodiment, since the silane monomer or oligomer thereof exhibits a sufficient fixing force even when only a small amount is used, the use of the silane monomer or oligomer thereof as a binder allows the exposed areas of the fixed virus inactivating fine particles to be increased. Therefore, the probability of contact of viruses adhering to the surface of the mask 100 with the virus inactivating fine particles can be higher than that when the virus inactivating fine particles are fixed to the filter member 1 using a binder such as a synthetic resin other than the silane monomer and oligomer thereof. The viruses can thereby be effectively inactivated even by using a small amount of the virus inactivating fine particles.

Since the virus inactivating fine particles are firmly fixed to the filter member 1 by the chemical bonds with the silane monomer or oligomer thereof, the amount of the virus inactivating fine particles falling off the filter member 1 is significantly reduced as compared to that when the particles are coated and fixed with, for example, a general binder component. Therefore, the mask 100 of the present embodiment can maintain its virus inactivating effect for a longer time. The virus inactivating fine particles may be held by a condensation reaction, amide bonds, hydrogen bonds, ion bonds, van der Waals forces, or physical adsorption. This can be achieved by selecting an appropriate silane monomer to be used.

In the first embodiment, no particular limitation is imposed on the form of holding the virus inactivating fine particles on the filter member, and the form may be appropriately selected by a person skilled in the art. For example, the respective fine particles may be scattered on the filter member 1. The inorganic fine particles may be held as inorganic fine particle aggregates arranged two- or three-dimensionally. More specifically, the virus inactivating fine particles may be held, for example, in a dot, island, or thin-film form. When the virus inactivating fine particles are held as three-dimensional aggregates, they include particles bonded to the filter member 1 through the silane monomer or oligomer thereof (such particles are referred to as virus inactivating fine particles a) and particles bonded to the filter member 1 through at least the virus inactivating fine particles a.

Preferably, the virus inactivating fine particles are held on the filter member 1 as three-dimensional aggregates because a large number of fine irregularities are formed on the surface of the filter member 1 and the adhesion of dust and the like to the mask body 10 is suppressed by the irregularities. The suppression of the adhesion of dust and the like allows the virus inactivating effect of the mask 100 to be maintained for a longer time.

In the mask 100 of the first embodiment, a functional material optionally used, in addition to the virus inactivating fine particles, to impart a desired function to the mask 100 may be held on the surfaces of the filter member 1 constituting the mask body 10. Examples of the functional material include other antiviral agents, antimicrobial agents, antifungal agents, anti-allergen agents, and catalysts. Such a functional material may be fixed to the filter member 1, the virus inactivating fine particles, and the like through, for example, a binder. As in the virus inactivating fine particles, the functional material may be bonded to the filter member 1 through chemical bonds between the silane monomer or oligomer bonded to the surface of the functional material and the surface of the filter.

A person skilled in the art can appropriately set the amount of the virus inactivating fine particles held by the mask 100 of the first embodiment, in consideration of the use purpose and application of the mask and of the size of the fine particles. The amount of the virus inactivating fine particles held by the mask body 10 is preferably 1.0 percent by mass to 80.0 percent by mass to the sum total of mass of the substances held on the filter member 1 constituting the mask body 10 and more preferably 5.0 percent by mass to 60.0 percent by mass. When the amount of the virus inactivating fine particles is less than 1.0 percent by mass, the virus inactivating activity is lower than that when the amount falls within the above range. When the amount is larger than 80.0 percent by mass, the virus inactivating effect is not largely different from that when the amount falls within the above range. Further, the binding properties of the oligomer formed by the condensation reaction of the silane monomer are reduced, and therefore the virus inactivating fine particles fall off the filter member 1 more easily than when the amount falls within the above range. In the present description, the substances held on the filter member 1 can include a silane monomer or oligomer thereof.

A description will next be given of the filter member 1 holding the virus inactivating fine particles. In the first embodiment, no particular limitation is imposed on the form of the filter member 1, so long as it has breathability. The virus inactivating material may be held on surfaces with various forms. Examples of the filter member 1 include fabrics such as woven fabrics, knitted fabrics, and nonwoven fabrics, and mixed-paper sheets that are formed of materials, for example, various resins, synthetic fibers, natural fibers such as cotton, hemp, and silk, and Japanese paper obtained from natural fibers, that can be chemically bonded to the silane monomer on the virus inactivating fine particles at the surface of the filter member 1. Specific examples of such materials of the filter member 1 include polyester, polypropylene, polyethylene terephthalate, nylon, acrylic, polyacrylic acid, polymethyl methacrylate, rayon, acetate, triacetate, cotton, hemp, wool, silk, and bamboo. A person skilled in the art can appropriately set the shape of the filter member 1 according to the shape of the mask body 10.

The manufacture method of the mask 100 of the first embodiment that has the virus inactivating fine particles held thereon will next be described more specifically.

First, at least one is selected from platinum(II) iodide, palladium(II) iodide, copper(I) iodide, silver(I) iodide, and copper(I) thiocyanate, and the selected material is pulverized into particles of the order of sub-micrometers to micrometers using, for example, a jet mill, a hammer mill, a ball mill, or a vibration mill to obtain virus inactivating fine particles. No particular limitation is imposed on the pulverization, and any of wet and dry processes can be used.

Next, the pulverized virus inactivating fine particles are dispersed in a solvent such as water, methanol, ethanol, MEK, acetone, xylene, or toluene. At this point, other materials such as a binder component including a silane monomer or an oligomer thereof and functional materials may be mixed with the dispersion. Then a dispersing agent such as a surfactant is added if necessary, and the resultant mixture is dispersed and pulverized using an apparatus such as a bead mill, a ball mill, a sand mill, a roll mill, a vibration mill, or a homogenizer, thereby preparing a slurry containing the virus inactivating fine particles dispersed therein. When the slurry is prepared in the manner described above, the particle diameter of the virus inactivating fine particles is reduced, and these particles are arranged on the surface of the filter member 1 constituting the mask body 10 without excessively large gaps formed between the particles. The particle density of the virus inactivating fine particles can thereby be increased, and accordingly, a high virus inactivating ability can be achieved.

The slurry prepared as described above is applied to the surface of the filter member 1 using a method such as a dipping method, a spraying method, a roll coating method, a bar coating method, a spin coating method, a gravure printing method, an offset printing method, a screen printing method, or an inkjet printing method. If necessary, the solvent is removed by, for example, heating and drying. Next, the functional groups on the surface of the filter member 1 are chemically bonded to the silane monomer through graft polymerization by re-heating or graft polymerization by irradiation with infrared rays, ultraviolet rays, an electron beam, or radioactive rays such as γ rays. During graft polymerization, the virus inactivating fine particles are bonded to each other through the silane monomer. By conducting such a process, the filter member 1 that holds the virus inactivating fine particles having a virus inactivating ability can be obtained.

Next, a mask body 10 is formed using the filter member 1. The formed mask body 10 is pleated, and rubber cords 2 are sewed to obtain the mask 100 of the first embodiment. In this process, the three filter members 1 are stacked and sewed to each other, and an integrated stacked body is thereby obtained and used as the mask body 10.

With the above-described mask 100 of the first embodiment, various viruses can be inactivated regardless of the types of genomes and whether or not the viruses have an envelope. Examples of the viruses include rhinoviruses, polioviruses, foot and mouth disease viruses, rotaviruses, noroviruses, enteroviruses, hepatoviruses, astroviruses, sapoviruses, hepatitis E viruses, type A, B, and C influenza viruses, parainfluenza viruses, mumps viruses, measles viruses, human metapneumoviruses, RS viruses, Nipah viruses, Hendra viruses, yellow fever viruses, dengue viruses, Japanese encephalitis viruses, West Nile viruses, hepatitis B and C viruses, eastern and western equine encephalitis viruses, O'nyong-nyong viruses, rubella viruses, Lassa viruses, Junin viruses, Machupo viruses, Guanarito viruses, Sabia viruses, Crimean-Congo hemorrhagic fever viruses, sandfly fever viruses, Hantaviruses, Sin Nombre viruses, rabies viruses, Ebola viruses, Marburg viruses, bat lyssaviruses, human T-lymphotropic viruses, human immunodeficiency viruses, human coronaviruses, SARS coronaviruses, human parvoviruses, polyoma viruses, human papilloma viruses, adenoviruses, herpes viruses, Varicella zoster viruses, EB viruses, cytomegaloviruses, smallpox viruses, monkeypox viruses, cowpox viruses, molluscipox viruses, and parapoxviruses.

In the mask 100 of the first embodiment, viruses can be inactivated even in the presence of, in addition to the viruses, lipids and proteins resulting from, for example, the adhesion droplets.

Therefore, with the mask 100 of the first embodiment, the viruses adhering to the mask can be inactivated. Therefore, the wearer can be prevented from viral infection, and the spread of viruses from an infected person can be suppressed. In addition, the occurrence of secondary infection due to contact with a used mask 100 can be reduced.

Second Embodiment

In a mask 100 of a second embodiment, in addition to the virus inactivating fine particles (hereinafter may be referred to as first inorganic fine particles), second inorganic fine particles used as additional fine particles are held on the filter members 1. In the second embodiment, the second inorganic fine particles together with the first inorganic fine particles form inorganic fine particle aggregates in which the inorganic fine particles are arranged two- or three-dimensionally. In other words, in the second embodiment, the inorganic particle aggregates containing the first inorganic fine particles and the second inorganic fine particles are held on the filter members 1. Structures common to those in the first embodiment are denoted by the same reference numerals, and the description will be omitted.

The second inorganic fine particles are bonded to the filter member 1 through a silane monomer or oligomer thereof and also are bonded to each other through the silane monomer or oligomer thereof. Therefore, in the second embodiment, the first inorganic fine particles serving as virus inactivating fine particles are bonded to the filter member 1 and the second inorganic fine particles through the silane monomer or oligomer thereof and are held on the filter member 1. In the second embodiment, the first inorganic fine particles are held on the filter member 1 so as to be entangled with groups of the second inorganic fine particles bonded to each other through the silane monomer or oligomer thereof. Therefore, the first inorganic fine particles are prevented from falling off the filter member 1 not only by the chemical bonds but also physically. In the mask of the second embodiment, the virus inactivating fine particles are more effectively prevented from falling off as compared to those in the mask of the first embodiment. Therefore, the virus inactivating ability can be maintained for a longer time.

In the second embodiment, the groups of the second inorganic fine particles that are bonded to each other through the silane monomer prevent the first inorganic fine particles from falling off the filter member 1. Therefore, the first inorganic fine particles may not form bonds with the second inorganic fine particles and the filter member through the silane monomer.

In the mask 100 of the second embodiment, the first inorganic fine particles serving as the virus inactivating fine particles are bonded to the second inorganic fine particles and the filter member through the silane monomer and oligomer thereof, and accordingly, the surfaces of the first inorganic fine particles are exposed, as in the first embodiment. Therefore, the probability of contact of viruses adhering to the surface of the mask 100 with the virus inactivating fine particles can be made higher than that when the virus inactivating fine particles are fixed to the filter member 1 using, for example, a general binder, so that the viruses can be effectively inactivated even by using a small amount of the virus inactivating fine particles.

No particular limitation is imposed on the second inorganic fine particles according to the second embodiment, so long as they can be bonded to the silane monomer or oligomer thereof, and a person skilled in the art can select appropriate second inorganic fine particles. Specifically, nonmetal oxides, metal oxides, metal composite oxides, nitrides, carbides, silicates, and mixtures thereof can be used. The second inorganic fine particles may be amorphous or crystalline. Examples of the nonmetal oxides include silicon oxide. Examples of the metal oxides include magnesium oxide, barium oxide, barium peroxide, aluminum oxide, tin oxide, titanium oxide, zinc oxide, titanium peroxide, zirconium oxide, iron oxide, iron hydroxide, tungsten oxide, bismuth oxide, indium oxide, gibbsite, boehmite, diaspore, antimony oxide, cobalt oxide, niobium oxide, manganese oxide, nickel oxide, cerium oxide, yttrium oxide, and praseodymium oxide. Examples of the metal composite oxides include barium titanium oxide, cobalt aluminum oxide, zirconium lead oxide, niobium lead oxide, $TiO_2$—$WO_3$, $AlO_3$—$SiO_2$, $WO_3$—$ZrO_2$, $WO_3$—$SNO_2$, $CeO_2$—$ZrO_2$, In—Sn, Sb—Sn, Sb—Zn, In—Sn—Zn, $B_2O_3$—$SiO_2$, $P_2O_5$—$SiO_2$, $TiO_2$—$SiO_2$, $ZrO_2$—$SiO_2$, $Al_2O_3$—$TiO_2$, $Al_2O_3$—$ZrO_2$, $Al_2O_3$—CaO, $Al_2O_3$—$B_2O_3$, $Al_2O_3$—$P_2O_5$, $Al_2O_3$—$CeO_2$, $Al_2O_3$—$Fe_2O_3$, $TiO_2$—$ZrO_2$, $TiO_2$—$ZrO_2$—$SiO_2$, $TiO_2$—$ZrO_2$—$Al_2O_3$, $TiO_2$—$Al_2O_3$—$SiO_2$, and $TiO_2$—$CeO_2$—$SiO_2$. Examples of the nitrides include titanium nitride, tantalum nitride, and niobium nitride. Examples of the carbides include silicon carbide, titanium carbide, and niobium carbide. Examples of the adsorptive silicates include: synthetic zeolites such as zeolite A, zeolite P, zeolite X, and zeolite Y; natural zeolites such as clinoptilolite, sepiolite, and mordenite; layer silicate compounds such as kaolinite, montmorillonite, Japanese acid clay, and diatomaceous earth; and cyclosilicate compounds such as wollastonite and neptunite. Other examples include phosphate compounds such as tricalcium phosphate, calcium hydrogen phosphate, calcium pyrophosphate, calcium metaphosphate, and hydroxyapatite, activated carbon, and porous glass.

Particularly, when particles having the ability to adsorb proteins are used as the second inorganic fine particles, they can adsorb allergen proteins such as pollen and mites.

Therefore, the combined use of such particles with the above-described virus inactivating fine particles having the effect of denaturing proteins can provide a mask having not only the virus inactivating ability but also anti-allergen performance.

A person skilled in the art can appropriately set the diameter of the second inorganic fine particles, according to, for example, the use purpose and application of the mask and the diameter of the second inorganic fine particles. In consideration of the binding strength to the filter member 1, the diameter of the second inorganic fine particles is preferably 500 nm or smaller and more preferably 300 nm or smaller. As described above, a person skilled in the art can appropriately set the particle diameter of the second inorganic fine particles. However, because of the same reason as that for the virus inactivating fine particles, the diameter is preferably 1 nm or larger.

The manufacture method of the mask 100 of the second embodiment that has virus inactivating fine particles held thereon will next be described more specifically.

First, as in the first embodiment, at least one is selected from platinum(II) iodide, palladium(II) iodide, copper(I) iodide, silver(I) iodide, and copper(I) thiocyanate, and the selected material is pulverized into particles of the order of micrometers using, for example, a jet mill, a hammer mill, a ball mill, or a vibration mill to obtain virus inactivating fine particles. No particular limitation is imposed on the pulverization, and any of wet and dry processes can be used.

Next, the pulverized virus inactivating fine particles are mixed with the second inorganic fine particles to which the silane monomer has been bonded through dehydration condensation, and the mixture is dispersed in a solvent such as water, methanol, ethanol, MEK, acetone, xylene, or toluene. In addition to the virus inactivating fine particles and the second inorganic fine particles to which the silane monomer has been bonded, other materials such as a binder component and functional materials may be added to the solvent at this point. Then a dispersing agent such as a surfactant is added if necessary, and the resultant mixture is dispersed and pulverized using an apparatus such as a bead mill, a ball mill, a sand mill, a roll mill, a vibration mill, or a homogenizer to prepare a slurry containing the virus inactivating fine particles and the second inorganic fine particles dispersed therein. When the slurry is prepared in the manner described above, the diameters of the virus inactivating fine particles and the second inorganic fine particles are reduced, and the first virus inactivating fine particles and the second inorganic fine particles are arranged on the surface of the filter member 1 constituting the mask body 10 without excessively large gaps formed between the particles. The particle density of the virus inactivating fine particles can thereby be increased, and the groups of the second inorganic fine particles can be more firmly fixed to the surface of the filter member 1 constituting the mask body 10. Therefore, a high virus inactivating ability can be achieved, and the virus inactivating ability can be maintained for a longer time.

The chemical bonds between the second inorganic fine particles and the silane monomer can be formed by an ordinary method. In one exemplary method, the silane monomer is added to a dispersion, and the resultant dispersion is heated under reflux to allow the silane monomer to be bonded to the surfaces of the second inorganic fine particles through a dehydration-condensation reaction to thereby form thin films made of the silane monomer. In another exemplary method, the silane monomer is added to a dispersion that has been subjected to pulverization to reduce the size of the particles, or alternatively, the silane monomer is added to a dispersion of the second inorganic fine particles, and the resultant dispersion is subjected to pulverization to reduce the size of the particles. Then the solid and liquid are separated from each other, and the separated solid is heated at 100° C. to 180° C. to allow the silane monomer to be bonded to the surfaces of the second inorganic fine particles through a dehydration-condensation reaction. The resultant particles are pulverized and then re-dispersed.

In the methods described above, the amount of the silane monomer to be added to the dispersion depends on the average particle diameter and material of the second inorganic fine particles. However, when the amount is 3 percent by mass to 30 percent by mass based on the mass of the second inorganic fine particles, the mutual bonding strength between the second inorganic fine particles and the bonding strength between the groups of the second inorganic fine particles and the filter member constituting the mask body 10 of the present invention do not cause any practical problems. Even after the silane monomer and the like are bonded to the first inorganic fine particles, the surfaces of the first inorganic fine particles are exposed sufficiently. In addition, an excess of silane monomer that is not involved in the bonding may be present.

The description of the method of manufacturing the mask 100 of the second embodiment will be continued. As in the first embodiment, the above-prepared slurry is applied to the surface of the filter member 1 using a method such as a dipping method, a spraying method, a roll coating method, a bar coating method, a spin coating method, a gravure printing method, an offset printing method, a screen printing method, or an inkjet printing method. If necessary, the solvent is removed by heating and drying and the like. Next, the functional groups on the surface of the filter member 1 are chemically bonded, through graft polymerization by re-heating or graft polymerization by irradiation with infrared rays, ultraviolet rays, an electron beam, or radioactive rays such as γ rays, to the silane monomer bonded to the surfaces of the second inorganic fine particles which face the surface of the filter member 1. At the same time, the silane monomers on the surfaces of the second inorganic fine particles are chemically bonded to each other to form an oligomer. At the same time, the virus inactivating fine particles are bonded to the second inorganic fine particles through the silane monomer. When a binder (another silane monomer) is added, the virus inactivating fine particles are bonded to the second inorganic fine particles and the mask body 10 through the silane monomer and formed oligomer. By conducting such a process, the virus inactivating fine particles having a virus inactivating ability are surrounded by the groups of the second inorganic fine particles, and the filter member 1 holding the virus inactivating fine particles on the surface thereof is thereby obtained.

Next, the mask body 10 is formed using the filter members 1, and the mask body 10 is pleated. Then rubber cords 2 are sewed onto the mask body 10 to obtain the mask 100 of the first embodiment. In this process in the second embodiment, as in the first embodiment, three filter members 1 are stacked and sewed to each other, and an integrated stacked body is thereby obtained and used as the mask body 10.

In the above description, the silane monomer is bonded to the second inorganic fine particles in advance, but this mode is not a limitation. The virus inactivating fine particles, second inorganic fine particles to which no silane monomer has been bonded, and the silane monomer may be dispersed in a dispersion medium. A person skilled in the art may appropriately set the amount of the silane monomer added. As in the above description, the amount added may be, for example, 3 percent by mass to 30 percent by mass based on the mass of the second inorganic fine particles. In the above range of addition, the mutual bonding strength between the second inorganic fine particles and the bonding strength between the groups of the second inorganic fine particles and the filter member constituting the mask body 10 of the present invention do not cause any practical problems. Even after the silane monomer is bonded to the second inorganic fine particles, the surfaces of the first inorganic fine particles are exposed sufficiently.

Other Embodiments

Figure 3:
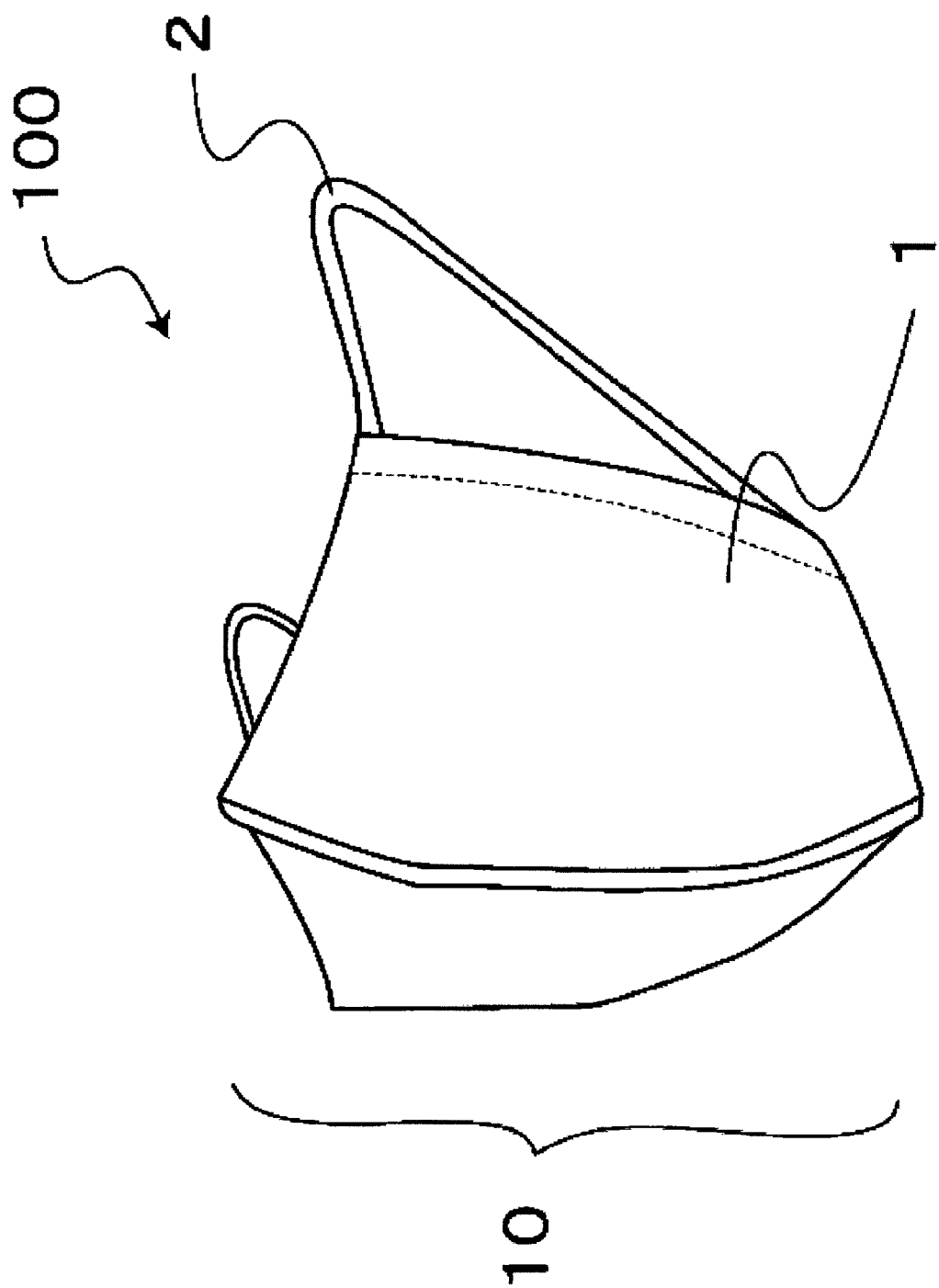
FIG. 3 is a perspective view of a mask of another embodiment.
Figure 4:
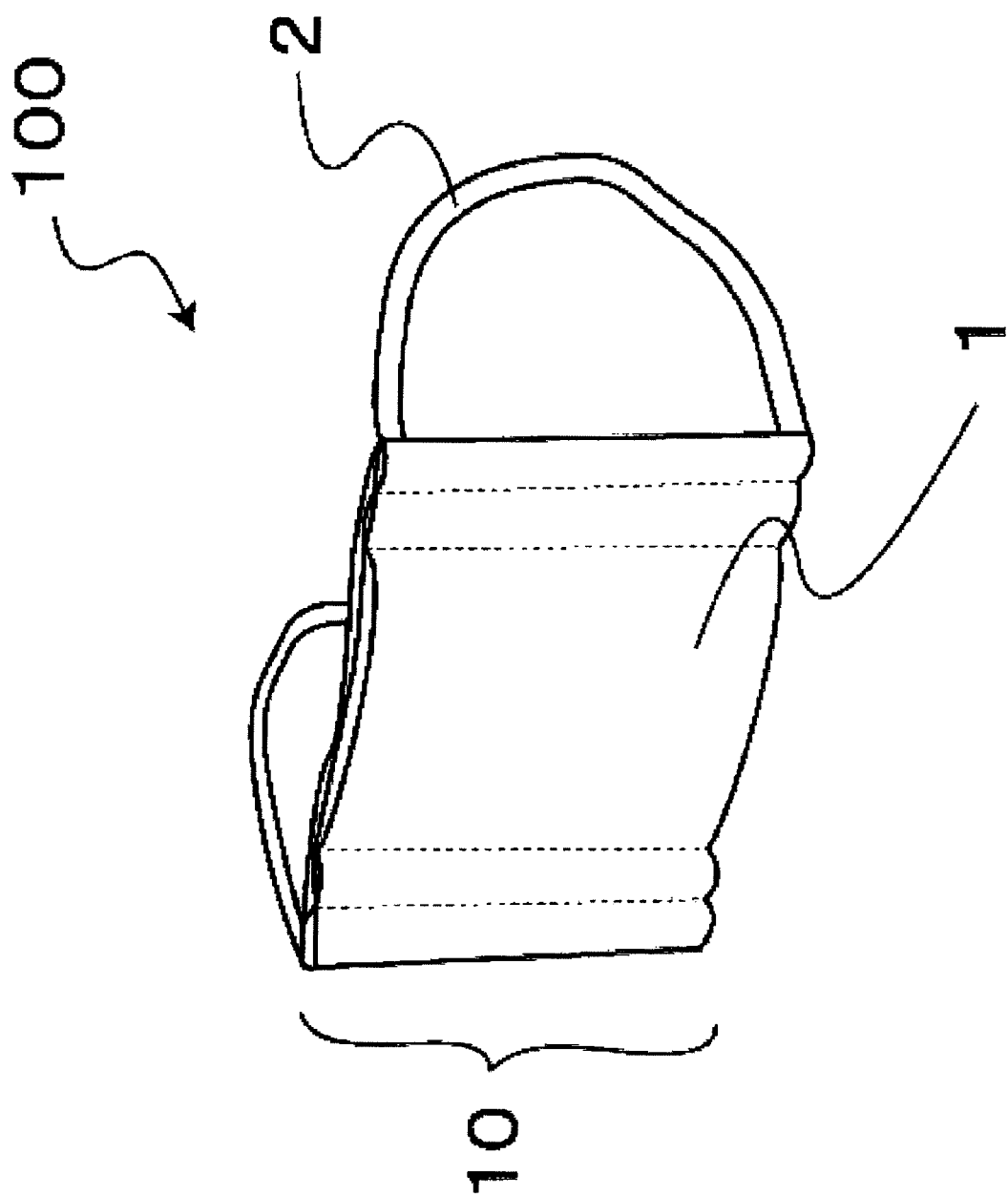
FIG. 4 is a perspective view of a mask of another embodiment.

The masks 100 of the first and second embodiments have been described above. However, the present invention is not limited thereto, and other embodiments are, of course, possible. For example, the shape of the mask 100 is not limited to the type shown in FIG. 1. As shown in FIG. 3, the mask may have a shape obtained by stamping using a hot press. In addition, the invention can be applied to a gauze mask shown in FIG. 4.

The filter members 1 stacked may have different functions. For example, filter members 1 that are to be located on the outermost and innermost sides during wearing of the mask may be subjected to antibacterial and deodorizing treatment to prevent bad odors and the propagation of bacteria. In the first and second embodiments, the mask body is composed of a plurality of filter members 1. Of course, the mask body can be composed of one filter member 1. However, when a plurality of filter members 1 are stacked to constitute a mask body 10, viruses can be more efficiently inactivated as compared to when one filter member 1 is used to form a mask body.

In another embodiment, a filter member having a function or configuration different from those of the above-described filter members 1 having the virus inactivating fine particles held thereon may be stacked on these filter members 1 to constitute a mask body 10. For example, the filter members 1 having the virus inactivating fine particles held thereon are disposed on the outermost and innermost sides when the mask is worn, and a filter member, such as an electret, having high dust collecting efficiency (hereinafter may be referred to as an electret filter member) is disposed between these filter members 1. In other words, this mask body 100 is configured such that the electret filter member and the filter members 1 are stacked so as to be sandwiched between the two filter members 1, and the virus inactivating fine particles are held at least on the filter members disposed on the outermost and innermost sides when the mask is worn. With this configuration, even when the filter members have a low unit weight, which can facilitate respiration, sufficient dust collecting efficiency can be obtained. The filter members 1 are stacked on the electret filter member so as to be located on the outermost and innermost sides. Therefore, viruses in droplets sprayed from carriers of the viruses and viruses floating in the air can be collected and inactivated by the outermost filter member 1, and viruses present in droplets from the mouth and nose of the wearer can be collected and inactivated by the innermost filter member 1 facing the mouth and nose.

When the mask body 10 includes a plurality of stacked filter members 1, it is preferable that at least the filter member 1 having the inorganic particles held thereon is disposed on the innermost side when the mask is worn. With this configuration, viruses present in droplets from the mouth and nose of the wearer can be inactivated, and the virus inactivating effect can be improved by moisture contained in the breath of the wearer. In a conventional mask in which a material having a virus inactivating ability is different from the virus inactivating fine particles of the present embodiment, the inactivating effect is significantly reduced by lipids and proteins originating from the wearer, when a filter member having such a material held thereon is disposed on the innermost side. However, in the mask of the present invention in which the virus inactivating fine particles held thereon can maintain its inactivating ability even in the presence of lipids and proteins, when the filter member holding the virus inactivating fine particles is disposed at least on the innermost side, the virus inactivating effect can be enhanced.

When the mask body 10 includes a plurality of filter members 1 stacked, at least the filter member disposed on the outermost side when the mask is worn may hold the virus inactivating fine particles thereon. With this configuration, viruses in droplets sprayed from carriers of the viruses and viruses floating in the air can be inactivated on the outermost side. Therefore, even if a hand comes into contact with the surface of the mask when the mask is worn or removed, secondary infection is less likely to occur. It is more preferable that the filter members holding the virus inactivating fine particles are disposed at least on the outermost and innermost sides when the mask is worn, because the virus inactivating effect can be improved and also viruses in droplets and viruses floating in the air can be inactivated.

In the first embodiment, the virus inactivating fine particles are held on the outer surfaces of the filter members through the silane monomer or oligomer thereof. However, the virus inactivating fine particles may be held on the mask body in a different manner. For example, the virus inactivating fine particles may be held on the filter member 1 through a binder component. No particular limitation is imposed on the binder component so long as it has high adhesion to the base material (the material of the filter members 1). Examples of the usable material include synthetic resins such as polyester resins, amino resins, epoxy resins, polyurethane resins, acrylic resins, water-soluble resins, vinyl-based resins, fluoro resins, silicone resins, cellulosic resins, phenolic resins, xylene resins, and toluene resins; and natural resins such as castor oil and drying oils for example, linseed oil and tung oil.

In the first and second embodiments, the virus inactivating fine particles are held on the surfaces of the filter members, but this is not a limitation. The virus inactivating fine particles may be held in the mask as a whole. For example, the virus inactivating fine particles may be held so as to be surrounded by the fibers constituting the filter members 1.

The present invention will next be specifically described by way of Examples. However, the present invention is not limited only to these Examples.

EXAMPLES (Examination of Virus Inactivating Ability of Virus Inactivating Fine Particles)

Before the effects of the mask of the present invention were examined, the virus inactivating ability of the virus inactivating fine particles formed of any of platinum(II) iodide, palladium(II) iodide, silver(I) iodide, copper(I) iodide, and copper(I) thiocyanate and to be held on the filter member 1 of the mask body 10 was examined. The examination was performed using a hemagglutination (HA) inhibition assay generally used to measure the titer of a virus. An influenza virus (influenza A/Kitakyusyu/159/93(H3N2)) cultured in NDCK cells was used as a subject virus.

More specifically, a two-fold dilution series of a virus solution was prepared in a plastic-made 96 well plate. Then 50 µL of a 0.5% chicken blood cell suspension was added to each of the wells. The wells were allowed to stand at 4° C. for 1 hour, and then an HA titer was determined. The determined HA titer was 128. Next, virus inactivating fine particles was diluted to 10 percent by mass with phosphate buffered saline. 450 µL, of the virus solution was added to 450 µL of the diluted solution, and the resultant solution was allowed to react at room temperature for 10 minutes under stirring using a micro-tube rotator. The powder was precipitated by centrifugation, and 150 µL of the supernatant was collected and used as a sample. A two-fold dilution series of the obtained sample solution was prepared. Then an equal amount of a 0.5% chicken blood cell suspension was added. The resultant solutions were allowed to stand at 4° C. for 60 minutes, and an HA titer was determined. The results are shown in Table 1.

TABLE 1

| | CONCENTRATION OF INACTIVATING AGENT | |
|---|---|---|
| | 0 PERCENT BY MASS | 10 PERCENT BY MASS |
| PLATINUM(II) IODIDE | 128 | <2 |
| PALLADIUM(II) IODIDE | 128 | 4 |
| SILVER(I) IODIDE | 128 | 64 |
| COPPER(I) IODIDE | 128 | 16 |
| COPPER(I) THIOCYANATE | 128 | 2 |

As can be seen from the above results, the virus inactivating fine particles formed of any of platinum(II) iodide, palladium(II) iodide, silver(I) iodide, copper(I) iodide, and copper(I) thiocyanate were found to have the ability to inactivate the influenza virus with an HA titer of 2 to 64.

(Production of Filter Members 1 Having the Effect of Inactivating Various Viruses)

Example 1

A commercially available powder of copper (I) iodide (product of Wako Pure Chemical Industries, Ltd., Wako 1st grade) was used as virus inactivating fine particles having a virus inactivating ability and was pulverized into an average particle diameter of 170 nm using a dry pulverizer, Nano Jetmizer (product of Aishin Nano Technologies CO., Ltd.). The pulverized copper(I) iodide fine particles were added to ethanol in an amount of 2.0 percent by mass, and tetramethoxy silane (KBM-04, product of Shin-Etsu Chemical Co., Ltd.) was further added in an amount of 0.4 percent by mass. The mixture was pre-dispersed using a homogenizer for 5 minutes to prepare a slurry. The average particle diameter as used herein is a volume average particle diameter.

Next, a rayon nonwoven fabric (product of SHINWA Corp.) of 20 g/m$^2$ was immersed in the prepared slurry. Any excess of the slurry was removed, and the nonwoven fabric was dried at 120° C. for 10 minutes to obtain a filter member 1 having a virus inactivating effect.

Example 2

100.0 g of a commercially available powder of copper(I) thiocyanate (product of Wako Pure Chemical Industries, Ltd., chemical use) used as virus inactivating fine particles (first inorganic fine particles) was pre-dispersed in 900.0 g of ethanol and then pulverized and dispersed using a bead mill to obtain a slurry having an average particle diameter of 104 nm.

Next, methacryloxypropyltrimethoxy silane (KBM-503, product of Shin-Etsu Chemical Co., Ltd.), a silane monomer having an unsaturated bonding part, was subjected to dehydration-condensation by an ordinary method to covalently-bond the silane to the surfaces of zirconium oxide particles (PCS, product of Nippon Denko Co., Ltd.), and the resultant particles were used as second inorganic fine particles. 100.0 g of the second inorganic fine particles were pre-dispersed in ethanol and were pulverized and dispersed using a bead mill to obtain a slurry having an average particle diameter of 15.1 nm. The average particle diameter as used herein is a volume average particle diameter.

The above two types of slurries were mixed in a mixing ratio of 40 percent by mass of the copper thiocyanate dispersion and 60 percent by mass of the zirconium oxide particle dispersion, and ethanol was added to the mixture such that the concentration of the solid content was adjusted to 3 percent by mass (hereinafter the resultant slurry is referred to as a mixed slurry).

Next, tetramethoxy silane (KBM-04, product of Shin-Etsu Chemical Co., Ltd.) was added to the mixed slurry in an amount of 0.3 percent by mass, and a rayon nonwoven fabric (product of KURARAYKURAFLEX Co., Ltd.) of 18 g/m$^2$ was dipped with the resultant mixture and then dried to obtain a filter member 1 having a virus inactivating effect.

Example 3

40.0 g of a commercially available powder of copper (I) iodide (product of Wako Pure Chemical Industries, Ltd., Wako 1st grade) used as virus inactivating fine particles (first inorganic fine particles) having a virus inactivating ability and 60.0 g of zirconium oxide particles (product of Nippon Denko Co., Ltd.) used as second inorganic fine particles were pre-dispersed in 900.0 g of ethanol. These particles were pulverized and dispersed using a bead mill to obtain a slurry containing copper(I) iodide fine particles having an average particle diameter of 205 nm and zirconium oxide fine particles having an average particle diameter of 37 nm. Ethanol was added to the obtained slurry such that the concentration of the solid content was adjusted to 1 percent by mass. The average particle diameter as used herein is a volume average particle diameter.

Next, tetramethoxy silane (KBM-04, product of Shin-Etsu Chemical Co., Ltd.) was added to the above slurry in an amount of 0.3 percent by mass, and the particles were dispersed using a homogenizer. A rayon nonwoven fabric (product of KURARAYKURAFLEX Co., Ltd.) of 18 g/m$^2$ was impregnated with the resultant slurry and dried to obtain a filter member 1 having a virus inactivating effect.

Example 4

A commercially available powder of silver(I) iodide (product of Wako Pure Chemical Industries, Ltd., chemical use) was used as virus inactivating fine particles (first inorganic fine particles) having a virus inactivating ability. Methacryloxypropyltrimethoxy silane (KBM-503, product of Shin-Etsu Chemical Co., Ltd.), a silane monomer having an unsaturated bonding part, was subjected to dehydration-condensation by an ordinary method to covalently-bond the silane to the surfaces of zirconium oxide particles (product of Nippon Denko Co., Ltd.), and the resultant particles were used as second inorganic fine particles. 40.0 g of the powder of silver(I) iodide and 60.0 g of the second inorganic fine particles were pre-dispersed in 900.0 g of methanol, and these particles were pulverized and dispersed using a bead mill to obtain a slurry containing silver(I) iodide fine particles having an average particle diameter of 124.8 nm and zirconium oxide fine particles having an average particle diameter of 15.1 nm. Ethanol was added to the obtained slurry such that the concentration of the solid content was adjusted to 3 percent by mass. The average particle diameter as used herein is a volume average particle diameter.

Next, tetramethoxy silane was added to the slurry in an amount of 0.3 percent by mass, and a rayon nonwoven fabric (product of KURARAYKURAFLEX Co., Ltd.) of 18 g/m$^2$ was dipped with the resultant slurry and dried to obtain a filter member 1 having a virus inactivating effect.

Example 5

A commercially available powder of copper (I) iodide (product of Wako Pure Chemical Industries, Ltd., Wako 1st grade) was used as virus inactivating fine particles (first inorganic fine particles). Methacryloxypropyltrimethoxy silane (KBM-503, product of Shin-Etsu Chemical Co., Ltd.), a silane monomer having an unsaturated bonding part, was subjected to dehydration-condensation by an ordinary method to covalently-bond the silane to the surfaces of zirconium oxide particles (PCS, product of Nippon Denko Co., Ltd.), and the resultant particles were used as second inorganic fine particles. 40.0 g of the powder of copper (I) iodide and 60.0 g of the second inorganic fine particles were pre-dispersed in 900.0 g of ethanol, and these particles were pulverized and dispersed using a bead mill to obtain a slurry containing copper(I) iodide fine particles having an average particle diameter of 60 nm and methacryloxypropyltrimethoxy silane-coated zirconium oxide fine particles having an average particle diameter of 37 nm. Ethanol was added to the obtained slurry such that the concentration of the solid content was adjusted to 1 percent by mass. The average particle diameter as used herein is a volume average particle diameter.

Next, a rayon nonwoven fabric (product of KURARAYKURAFLEX Co., Ltd.) of 18 g/m$^2$ was dipped with the resultant slurry and dried to obtain a filter member 1 having a virus inactivating effect.

Example 6

A filter member 1 having a virus inactivating effect was obtained under the same conditions as in Example 5 except that tetramethoxy silane (KBM-04, product of Shin-Etsu Chemical Co., Ltd.) was added in an amount of 0.3 percent by mass to the slurry used in Example 5.

Comparative Example 1

A filter member of Comparative Example 1 was obtained under the same conditions as in Example 6 except that the virus inactivating fine particles used in Example 6 were not added.

Comparative Example 2

Only a rayon nonwoven fabric (product of KURARAYKURAFLEX Co., Ltd.) of 18 g/m$^2$ was used as a filter member of Comparative Example 2.

(Evaluation of Filter Members 1 Having Virus Inactivating Effect on Various Viruses)

In the measurement of the virus inactivating ability of the filter members, four types of viruses including influenza viruses A/yamagata/1/08 (H1N1), A/kitakyushu/159/93 (H3N2), and B/Bangkok/163/90, and a feline calicivirus F9 strain were used as subject viruses. A sample nonwoven fabric sheet (5 cm×5 cm) of one of Examples 1, 3, 5, and 6 and Comparative Examples 1 and 2 was placed on three untreated nonwoven fabric sheets, and the sheets were held with tweezers. 250 μL of an undiluted virus solution was placed into a commercially available solution administration and nasal-oral administration apparatus ("AAN shutto atomizer," product of Keytron, an apparatus that can spray liquid as droplets having a size corresponding to the size of oral-nasal droplets), and the entire amount of the virus solution was sprayed onto the nonwoven fabric from a distance of 10 cm. The sample sprayed with the virus solution was placed in a sterilized plastic petri dish. After sensitization for 60 minutes, 1 mL of a bouillon solution was added to wash the virus off. Then the reaction sample was diluted with an MEM diluting solution until $10^{-2}$ to $10^{-5}$ (ten-fold serial dilution), and 100 μL of the diluted sample solutions were inoculated on MDCK cells. After virus adsorption for 90 minutes, a 0.7% agar medium was placed thereon, and the virus was cultured at 34° C. in 5% of $CO_2$ for 48 hours in an incubator. After formalin-fixation and methylene blue staining were performed, the number of plaques formed was counted to compute the infectivity titer of the virus (PFU/0.1 mL, Log 10) (PFU: plaque-forming units), and the computed infectivity titer was compared with that of a control.

(Control)

A 5 cm square plastic film was used as a virus control instead of the test nonwoven fabric sheets.

TABLE 2

| | INFECTIVITY TITER OF VIRUS (PFU/0.1 ml, Log10) | | | |
|---|---|---|---|---|
| | INFLUENZA VIRUS | | | FELINE CALICIVIRUS F9 STRAIN |
| | TYPE A (H1N1) | TYPE A (H3N2) | TYPE B | |
| EXAMPLE 1 | <1 | <1 | <1 | <1 |
| EXAMPLE 3 | <1 | <1 | <1 | <1 |
| EXAMPLE 5 | <1 | <1 | <1 | <1 |
| EXAMPLE 6 | <1 | 1.3 | <1 | <1 |
| COMPARATIVE EXAMPLE 1 | 5.23 | 6.58 | 5.73 | 5.63 |
| COMPARATIVE EXAMPLE 2 | 5.62 | 6.67 | 5.85 | 5.94 |
| CONTROL | 6.61 | 6.68 | 6.94 | 6.02 |

(Evaluation of Virus Inactivating Effect in the Presence of Protein)

In the measurement of the virus inactivating ability of the filter members, BSA (bovine serum albumin) was added in an amount of 0.5 percent by mass, which was an estimated amount of proteins contained in saliva, to an undiluted solution of an influenza virus A/kitakyushu/159/93 (H3N2) and to an undiluted solution of a feline calicivirus F9 strain that were used as subject viruses. A sample nonwoven fabric sheet (5 cm×5 cm) was placed on three untreated nonwoven fabric sheets, and the sheets were held with tweezers. 250 μL of one of the undiluted virus solutions was placed into a commercially available solution administration and nasal-oral administration apparatus ("AAN shutto atomizer," product of Keytron, an apparatus that can spray liquid as droplets having a size corresponding to the size of oral-nasal droplets), and the entire amount of the virus solution was sprayed onto the nonwoven fabric from a distance of 10 cm. The sample sprayed with the virus solution was placed in a sterilized plastic petri dish. After sensitization for 60 minutes, 1 mL of a bouillon solution was added to wash the virus off. Then the reaction sample was diluted with an MEM diluting solution until $10^{-2}$ to $10^{-5}$ (ten-fold serial dilution), and 100 μL of the diluted sample solutions were inoculated on MDCK cells. After virus adsorption for 90 minutes, a 0.7% agar medium was placed thereon, and the virus was cultured at 34° C. in 5% of $CO_2$ for 48 hours in an incubator. After formalin-fixation and methylene blue staining were performed, the number of plaques formed was counted to compute the infectivity titer of the virus (PFU/0.1 mL, Log 10) (PFU: plaque-forming units), and the computed infectivity titer was compared with that of a control.

(Control)

A 5 cm square plastic film was used as a virus control instead of the test nonwoven fabric sheets.

TABLE 3

| | INFECTIVITY TITER OF VIRUS (PFU/0.1 ml, Log10) | |
|---|---|---|
| | INFLUENZA VIRUS | FELINE CALICIVIRUS |
| EXAMPLE 1 | <1 | <1 |
| EXAMPLE 2 | 1.95 | 2.01 |
| EXAMPLE 3 | <1 | <1 |
| EXAMPLE 4 | <1 | <1 |
| EXAMPLE 5 | <1 | <1 |
| EXAMPLE 6 | <1 | <1 |
| COMPARATIVE EXAMPLE 1 | 6.45 | 5.43 |
| COMPARATIVE EXAMPLE 2 | 6.53 | 5.71 |
| CONTROL | 6.90 | 5.90 |

As can be seen from the above results, the inactivating effect on the A type and B type influenza viruses was found in Examples 1, 3, 5, and 6. Particularly, in Examples 1, 3, and 5, the effect observed was very high, i.e., the inactivation ratio after 60 minutes was 99.9999% or higher. In Example 6, a small amount of the H3N2 virus remained non-inactivated. However, the inactivation ratio was very high (99.9996%). Even in the presence of the protein, similar results of 99.9999% or higher were obtained except for Example 2. Even in Example 2, the effect was as high as 99.99%. The mask of the present invention configured to include filter members having a virus inactivating ability can inactivate viruses once adhering to the mask in about 1 hour, which varies depending on the amount of the virus inactivating fine particles and the like. Therefore, the mask provided is not a single use mask and can be used for a long time.

REFERENCE SIGNS LIST

100: mask
10: mask body
1: filter member
2: rubber cord
3: band-shaped wire
4: pleat

The invention claimed is:

1. A mask capable of inactivating a virus adhering thereto, the mask comprising:

a mask body provided with a member used when the mask is worn;

first fine particles capable of inactivating the virus, wherein the first fine particles are selected from at least one of the group consisting of platinum(II) iodide, palladium(II) iodide, silver(I) iodide, copper(I) iodide, and copper(I) thiocyanate, and second fine particles which are solid inorganic fine particles without pores, wherein the second fine particles are directly bonded to each other through a first silane monomer and/or a first polymerization product of the silane monomer and are fixed to the mask body through chemical bonds with a second silane monomer and/or a second polymerization product of the silane monomer, wherein the first fine particles are entangled with the second fine particles, and are fixedly entangled without forming bonds with the second fine particles through any silane monomer and/or polymerization product of the silane monomer, and wherein the second fine particles are selected from the group consisting of titanium oxide, zinc oxide, titanium peroxide, zirconium oxide, iron oxide, iron hydroxide, tungsten oxide, indium oxide, niobium oxide, cerium oxide, $TiO_2$—$WO_3$, $WO_3$—$ZrO_2$, $CeO_2$—$ZrO_2$, $TiO_2$—$ZrO_2$, and mixtures thereof.

2. The mask according to claim 1, wherein the mask body includes a plurality of breathable filter members stacked in a thickness direction of the mask body, and the first fine particles are held by at least one of the plurality of breathable filter members constituting the mask body.

3. The mask according to claim 2, wherein the at least one of the plurality of breathable filter members is located on an innermost side when the mask is worn.

4. The mask according to claim 2, wherein the at least one of the plurality of breathable filter members is located on an outermost side when the mask is worn.

5. The mask according to claim 1, wherein the first fine particles are also bonded to the mask body with a third silane monomer and/or a third polymerization product of the silane monomer.

6. The mask according to claim 1, wherein an average diameter of the first fine particles is 1 nm or larger and smaller than 500 nm.

* * * * *